(12) United States Patent
Geiger et al.

(10) Patent No.: US 10,481,234 B2
(45) Date of Patent: Nov. 19, 2019

(54) THREE-DIMENSIONAL PRINTING OF PHANTOMS FOR MEDICAL IMAGING

(71) Applicant: Siemens Healthcare GmbH, Erlangen (DE)

(72) Inventors: Bernhard Geiger, Cranbury, NJ (US); Shaohua Kevin Zhou, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 218 days.

(21) Appl. No.: 15/532,615

(22) PCT Filed: Feb. 23, 2015

(86) PCT No.: PCT/US2015/017015
§ 371 (c)(1),
(2) Date: Jun. 2, 2017

(87) PCT Pub. No.: WO2016/137425
PCT Pub. Date: Sep. 1, 2016

(65) Prior Publication Data
US 2018/0267127 A1  Sep. 20, 2018

(51) Int. Cl.
| | |
|---|---|
| G01D 18/00 | (2006.01) |
| G09B 23/28 | (2006.01) |
| G09B 23/30 | (2006.01) |
| G01R 33/58 | (2006.01) |
| A61B 6/00 | (2006.01) |

(Continued)

(52) U.S. Cl.
CPC ............. *G01R 33/58* (2013.01); *A61B 6/582* (2013.01); *A61B 6/583* (2013.01); *A61B 6/584* (2013.01); *A61B 6/585* (2013.01); *A61B 8/587* (2013.01); *B29C 64/106* (2017.08);
(Continued)

(58) Field of Classification Search
CPC .......... A61B 6/582; A61B 6/583; A61B 6/584; A61B 6/585; A61B 8/587; B29C 64/106; B29C 64/112; B29C 64/386; B29C 64/393; B33Y 10/00; B33Y 50/00; B33Y 50/02; B33Y 80/00; G01D 18/00; G01R 33/58; G09B 23/28; G09B 23/286; G09B 23/30
USPC ............... 264/40.1, 308; 73/1.01; 250/252.1; 378/207; 434/267, 272
See application file for complete search history.

(56) References Cited

U.S. PATENT DOCUMENTS

| | | | |
|---|---|---|---|
| 2010/0202001 A1* | 8/2010 | Miller | A61B 6/583 |
| | | | 358/1.9 |
| 2014/0306126 A1* | 10/2014 | Betrouni | G09B 23/30 |
| | | | 250/492.1 |

FOREIGN PATENT DOCUMENTS

WO    WO2015003271    1/2015

OTHER PUBLICATIONS

International Search Report dated Oct. 28, 2015 in corresponding International Patent Application No. PCT/US2015/017015.
(Continued)

*Primary Examiner* — Leo B Tentoni

(57) ABSTRACT

A medical imaging phantom (18) is three-dimensionally printed (36). In one specific approach, three-dimensional printing (36) allows for any number of variations in phantoms (18). A library of different phantoms (18), different inserts, different textures, different densities, different organs, different pathologies, different sizes, different shapes, and/or other differences allows for defining a specific phantom (18) as needed. The defined phantom (18) is then printed (36) for calibration or other use in medical imaging.

19 Claims, 2 Drawing Sheets

(51) Int. Cl.
    *A61B 8/00*     (2006.01)
    *B29C 64/393*   (2017.01)
    *B29C 64/112*   (2017.01)
    *B29C 64/106*   (2017.01)
    *B29C 64/386*   (2017.01)

(52) U.S. Cl.
    CPC .......... *B29C 64/112* (2017.08); *B29C 64/386* (2017.08); *B29C 64/393* (2017.08); *G09B 23/286* (2013.01)

(56) References Cited

OTHER PUBLICATIONS

Wang Minjie et al: "3d printing method for freeform fabrication of optical phantoms simulating heterogeneous biological tissue", Progress in Biomedical Optics and Imaging, SPIE—International Society for Optical Engineering, Bellingham, WA, US, vol. 8945, Mar. 3, 2014 (Mar. 3, 2014), pp. 894509-894509.

Eric D Ehler et al: "Patient specific 3D printed phantom for IMRT quality assurance", Physics in Medicine and Biology, Institute of Physics Publishing, Bristol GB, vol. 59, No. 19, Sep. 10, 2014 (Sep. 10, 2014), pp. 5763-5773.

* cited by examiner

THREE-DIMENSIONAL PRINTING OF PHANTOMS FOR MEDICAL IMAGING

BACKGROUND

The present embodiments relate to phantoms for medical imaging. Medical imaging devices, such as computed tomography (CT), magnetic resonance (MR), ultrasound, fluoroscopy, positron emission tomography (PET), single photon emission computed tomography (SPECT), or x-ray, use phantoms to calibrate or for scientific investigation. The phantom provides known characteristics used as a ground truth to interpret scan results from the medical imaging system. This ground truth for comparison with imaging results may be particularly important for quantitative measuring with the medical imaging system, investigation of resolution of the medical imaging system, or to deal with imaging artifacts linked to specific densities or shapes.

The phantoms contain different materials with different densities, shapes, and/or thickness for measuring and comparing with scan results. For example, a phantom is gel with a suspended metal sphere or tube. Simple geometric structures of various sizes and/or densities suspended in other material may be easy to manufacture, so most phantoms have these simple structures. The same design may be used for many different medical imaging systems. However, the simplicity of design and/or limited variety in the available phantoms may limit the use of the phantoms. Designing more complex phantoms for a specific or limited use purpose may be overly costly.

BRIEF SUMMARY

By way of introduction, the preferred embodiments described below include methods, systems, instructions, and computer readable media for three-dimensional printing of a medical imaging phantom. In one specific approach, three-dimensional printing allows for any number of variations in phantoms. A library of different phantoms, different inserts, different textures, different densities, different organs, different pathologies, different sizes, different shapes, and/or other differences allows for defining a specific phantom as needed. The defined phantom is then printed and used for calibration or other use in medical imaging.

In a first aspect, a method is provided for three-dimensional printing of a medical imaging phantom. Using a database, a selection of an organ phantom from a library of organ phantoms is received. A three-dimensional printer prints the selected organ phantom. A medical imaging system is calibrated with the three-dimensionally printed organ phantom.

In a second aspect, a non-transitory computer readable storage medium has stored therein data representing instructions executable by a programmed processor for creating a medical imaging phantom for three-dimensional printing. The storage medium includes instructions for forming a three-dimensional print file for a medical imaging phantom from a library of artificial structures and organ structures, the artificial structures and organ structures including different patterns, different densities, and different pathologies, and outputting the three-dimensional print file to a three-dimensional printer.

In a third aspect, a system is provided for three-dimensional printing of a medical imaging phantom. A memory is configured to store a definition of the medical imaging phantom. A three-dimensional printer is configured to construct the medical imaging phantom from the definition. The medical imaging phantom is constructed by the three-dimensional printer.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Three-dimensional printing is used to create accurate phantoms. The phantoms may contain artificial structures and patterns or highly realistic details of actual human anatomy. For example, a library of phantoms is provided from image segmentation of actual scans of patients. The use of three-dimensional printing for phantoms provides for phantoms with specific anatomical details and/or pathologies.

The calibration may be improved by calibrating based on a phantom more closely representing the very anatomy to be imaged. Rather than relying on binary contrast in the phantom (e.g., two densities—one of the supporting material and the other of the artificial structure), any number of different densities may be provided by three-dimensional printing. A wide range of materials may be used for printing to obtain the desired densities, absorption or other characteristic depending on the imaging modality. The phantoms may be designed specifically for the type of imaging. For ultrasound phantoms, layer structures may be modeled in the phantom.

The phantoms may be created for purposes other than calibration. For example, a phantom representing an organ after surgical intervention (e.g., ablation) is designed and printed. The medical scan response from that phantom may be compared with the medical scan response from the patient after intervention to identify any discrepancy. Specific patterns or structures may be included in the phantom in order to study specific imaging phenomena, characteristics, or artifacts. Training and simulation over a wide variety of situations encountered in medical imaging may benefit from a purpose designed and constructed phantom. Three-dimensional printing may allow for cost effective, rapid, and convenient design and construction of medical imaging phantoms.

Three-dimensional printing may be expensive, especially for simple designs. The accuracy of three-dimensionally printed objects may be verified by direct measurements (size, diameter, volume) or by taking samples and using various measurements (density, x-ray absorption, chemical analysis). A phantom may be printed multiple times, and the printer repeatability may be measured and used as factor in the process (+/−x mm).

Figure 1:
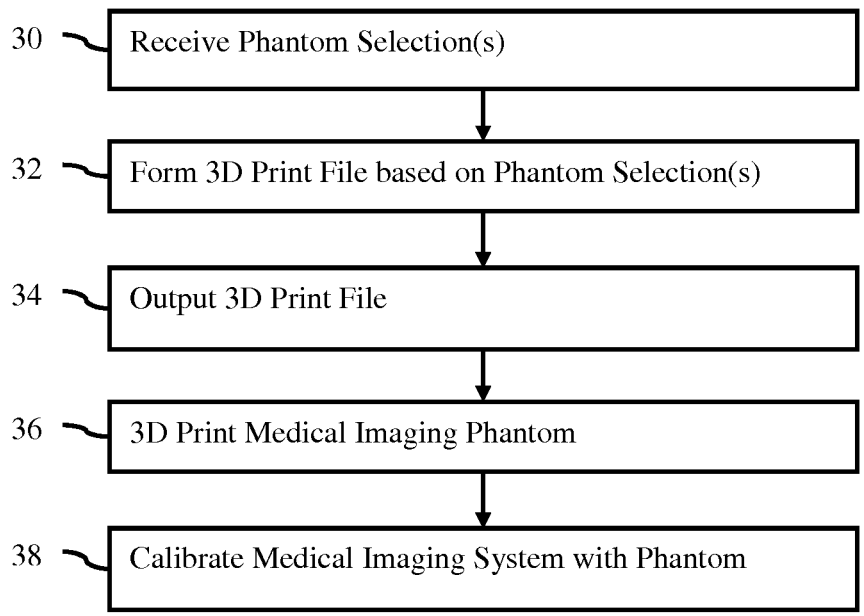
FIG. 1 is a flow chart diagram of one embodiment of a method for three-dimensional printing of a medical imaging phantom.

FIG. 1 shows a method for three-dimensional printing of a medical imaging phantom. The method is performed by the system of FIG. 2, the system of FIG. 3, a processor, a medical imaging system, a three-dimensional printer, a different system, or combinations thereof. For example, a computer, server, or other processor performs acts 30, 32, and 34. A three-dimensional printer performs act 36. A medical imaging system is used to perform act 38. The processor is part of or separate from the three-dimensional printer and/or medical imaging system. The method is performed in the order shown or a different order.

In general, the method is directed to the designing of the phantom using a library, printing of the phantom, and use of the phantom. In other embodiments, a single phantom design is available and printed rather than using a library. While act 38 shows calibration, other uses in medical imaging of the three-dimensionally printed phantom may be used. Additional, different, or fewer acts may be provided. For example, acts 30 and 32 are not performed. As another example, acts 36 and/or 38 are not performed. A service may provide print files for three-dimensional printing by others. In yet another example, act 36 is performed without other acts. Acts for configuring the three-dimensional printer may be provided.

In act 30, a phantom selection is received. A processor, such as part of a computer or server, presents a phantom or phantom related option. The phantom for medical imaging or phantom options are loaded from a database or other memory. The user selects the medical imaging phantom to be constructed.

A single phantom may be presented and selected. In other embodiments, the computer allows editing of the phantom design, so the selection received is the phantom as edited. Computer assisted design (CAD) or other editing tool is used to alter the model of the phantom. In yet other embodiments, a library of different phantoms is stored in the database. The selection received is selection of one of the different phantoms from the library. Additionally or alternatively, phantom options are stored in the database and presented. The user inputs one or more selections of different characteristics (i.e., options) of the phantom to design the selected phantom.

The user selects the desired phantom from the library. The phantom may be selected and constructed for specific purposes. Since the phantom may be created quickly and cost effectively, phantoms may be designed for specific purposes. For example, the user selects the phantom most similar to the anatomy to be imaged by the medical imaging system. The calibration may be refined for that anatomy. As another example, phantoms designed to test imaging characteristics, such as resolution, texture response, imaging artifacts, responsiveness to different settings, or other purposes may be designed. In another example, a phantom designed for user training on the medical imaging system is provided, such as for training for imaging specific organs or in specific situations. In yet another example, the phantom is designed and created for comparison with imaging results to verify the likely deformation or pathology for a particular patient (e.g., create more than one phantom with variations that may be possible for a patient, scan the phantoms, and identify the variation most similar to a patient based on scan response).

The library is specific to the imaging modality or may include phantoms useable in multiple different modalities. Different imaging modalities may have different requirements. For example, the density or absorption for x-ray (e.g., fluoroscopy, CT, or other x-ray-based modality) may be different than for MR, ultrasound, PET, or SPECT. A PET or SPECT phantom may include a radio nucleotide not needed in phantoms for other modalities. Some phantoms may be usable in more than one modality.

The library may include organ phantoms. The organ phantoms are phantoms that represent an organ. For example, a phantom representing the liver is provided. The library may include different phantoms for different types of organs. A phantom is provided for the liver, kidney, intestine, heart, lungs, muscle, bone, and/or for other anatomy. The user selection of the type of organ is a selection of the phantom.

Alternatively or additionally, more than one phantom may be provided to represent a given or same type of organ, such as the liver. For example, livers of different sizes are provided. As another example, livers with different deformities, lesions, densities, pathologies, locations of these differences, other differences in characteristic, or combinations thereof are provided. Each of the organs of the plurality of organ phantoms has a different pathology or other different characteristic. The user selection of the phantom of the same type of organ is a selection of the phantom. More refined selections, such as through design, may be provided.

The different organ phantoms are pre-designed and available for selection. Alternatively or additionally, one or more of the different organ phantoms are from medical scans of other patients. For example, archives of different patient organs or of the same organ with different pathologies are obtained. Using a mesh fitting or other approach, the organ of interest is segmented from the medical scan. The segmented organ may be converted into a phantom. In one approach, the conversion fits a mean or other model of the organ to the scan data, and the fit is then used to transform a three-dimensional printing design for the phantom to create the phantom based on the medical scan of a specific patient. Any of the approaches described in U.S. Published Patent Application 2016/0129637 (Ser. No. 14/539,051, filed Nov. 12, 2014) may be used. Other approaches for converting a segmentation from a medical scan into an organ phantom may be used. In this way, a plurality of different organ phantoms from different patients is created for a given organ.

The different organ phantoms may have characteristics specific to the type of medical imaging. For example, ultrasound reflects from layers or transitions in density. The organ phantom may have different density layers typically of layers found in the organ. By defining the organ phantom with layers of anatomic structure, the organ phantom may more accurately emulate ultrasound imaging of the actual organ. As another example, MR is responsive to the types of molecules. The organ phantoms for MR imaging may have materials with certain molecules distributed throughout the organ phantom to emulate a typical distribution in the organ being represented.

The selection may include selecting one or more characteristics of the organ phantom in addition to selecting a given organ phantom. The user may mix and match or edit characteristics of the organ phantom. The user selects size, thickness, densities, materials, pathologies, deformities, textures, or other aspects. Options are presented to the user for selection. More than one option may be selected, such as setting a size of the overall organ phantom and a size of an added lesion. The various selections are combined for selection of the organ phantom.

In one embodiment, user selection of one or more inserts is received. The user selects a natural or unnatural insert for the organ phantom. For example, the user selects from a library of inserts including spheres, tubes, or other geometrical structures. For natural inserts, the options include different lesions, deformities, or other naturally occurring pathologies. For unnatural insertions, structures with different shapes not naturally occurring in the organ (e.g., wires or spheres) are selected.

The density of the organ phantom may be set. Different organs have tissue of different density. The user may adjust the density for the organ phantom. Adjustments of specific parts may be received, such as increasing density in one region and decreasing or maintaining an initial or starting density in another region.

Many non-organ phantoms are currently used. The library may include non-organ phantoms as well or instead of the organ phantoms. Non-organ phantoms include non-natural structure, such as having a different density, including inserts with geometrical shapes not normally found in actual organs (e.g., sphere or straight tube), and/or having an overall or housing shape not modeled after an organ. For example, a cube, pyramidal, or spherical phantom with one or more non-natural inserts is provided for selection. Different non-organ phantoms may be provided for selection. Any of various characteristics may be selected for a given type of non-organ phantom.

The phantom that is selected is represented in a three-dimensional printing format. Alternatively, the phantom is a model, such as a computer assisted design model, mesh, medical scan segmentation, or other structure that is to be converted into a three-dimensional printing format.

In act 32, the processor forms a three-dimensional print file for the medical imaging phantom. The selected phantom is or is converted to a three-dimensional print file. For example, the library of artificial structures and organ structures, such as the different options (different organ representations, different types of organs, different patterns (e.g., textures), different densities, and different pathologies) includes transforms to the file format for printing for each option. As the user selects options, the resulting transform indicates the print file alteration. Alternatively, a different pre-made print file is stored for each possible combination of selections. In another embodiment, the final selected phantom is a model in a format for which a converter to a print file is available. For example, a CAD model results from the selection. The print file is formed by conversion of the CAD model to the print file format using a format converter.

The various received selections are used to form the print file. For example, a pathology selection (e.g., lesion) from the library is combined with an organ structure (e.g., liver) from the library. This combination defines the medical imaging phantom as a model of an organ with a pathology. The model created by the combination is converted to a print file format. Likewise, models from combinations of densities, patterns, artificial structures (e.g., unnatural), or other optional selections are converted to a print file format.

In act 34, a processor outputs the three-dimensional print file to a three-dimensional printer. The three-dimensional print model is output. The output is the selected or designed medical imaging phantom ready for three-dimensional printing. The output may be formatted for a specific 3D printer (e.g., G-code file) or 3D printers in general (STL file), such as having been sliced. Alternatively, the output is formatted as a computer assisted design file or other data structure that may be converted for 3D printing through slicing or other process.

The three-dimensional print model, as output, includes the medical imaging phantom as specified by the selections. The materials to be used and where in constructing the medical imaging phantom are defined. The various characteristics (e.g., density, including structures or patterns and locations thereof) are defined.

Other structure may be added to the phantom. For example, a base, legs or other supporting structure to hold the phantom level or in a desired orientation are added. The addition may be handled as a selection for designing the phantom, may be included in the phantoms to be selected, and/or may be added after the phantom is designed.

The output is to a three-dimensional printer. Alternatively, the output is to a memory or transfer over a network. In yet another embodiment, the output is to a workstation or computer assisted design system for display of a representation of the medical imaging phantom defined by the print file. The medical imaging phantom may be viewed to confirm readiness to print and/or for further manual alteration to correct any errors caused by conversion to the print file.

In act 36, the selected phantom is three-dimensionally printed. The three-dimensional printer receives the print file and constructs the organ or non-organ phantom. The print file may be reformatted or compiled into instructions for printing. Alternatively, the print file includes the compiled instructions. In response to the print file, the three-dimensional printer prints out a plastic, metal, ceramic, paper, and/or other material representation of the selected phantom.

Any three-dimensional printing may be used. For plastic or resin, a nozzle deposits material selected for the appropriate property (e.g., density) in a layer build-up. Different material may be deposited at different locations, such as depositing to provide different densities for different locations. For metal, a metal powder or sintered material is deposited. A laser or other heat source then causes the metal to bond together. Molecules, chemicals, liquids, or other material may be added to the material being deposited. For example with an x-ray phantom, iodine may be added to the plastic to be melted by the three-dimensional printer or after the melting. As the three-dimensional printer deposits material to represent blood regions (e.g., vessels), the iodine laced plastic is used. Plastic without iodine is used for other locations. Other three-dimensional printing techniques may be used.

The phantom may be changed from one type of three-dimensional printer to another while being constructed. For example, an organ phantom is constructed from plastic while spherical inserts are constructed from metal. The three-dimensional printer for the plastic creates a cavity for the metal. Before sealing the cavity with plastic, the partially constructed phantom is moved to the three-dimensional printer for metal for adding the insert. The phantom is then moved back for further deposition of plastic. Alternatively, a single three-dimensional printer may print using different processes.

The three-dimensional printing provides a phantom with the selected characteristics. Different materials are deposited at different locations to form a three-dimensional objects with the characteristics distributed as designed. For example, the layers emulating the organ tissue structure are created. These layers may be different than the layers used for depositing by the three-dimensional printer.

In act 38, the constructed medical imaging phantom is used to calibrate a medical imaging system. The three-dimensionally printed phantom, such as emulating an organ, is positioned in the medical imaging system and scanned. The scan results are compared against the known information for the phantom. For example, the phantom includes a tube with a known diameter. The scan may indicate a diameter measured by the imaging system that is different. The offset between actual and measured is used to set a value of a variable. This value corrects the measured diameter so that when the patient is scanned, the measurement is more accurate. Any now known or later developed calibration and calibration process may be used. The calibration may result in more accurate quantification by the medical imaging system.

The phantom is designed and constructed for this calibration. Since three-dimensional printing is used, the phantom may be designed and constructed for specific calibrations. For example, the medical imaging system is to be used for measuring a given vessel in one or more patients. The phantom may include structure at the typical size and/or shape of the given vessel. The resulting calibration may be more accurate due to the similarity of the calibrating structure and the vessel to be measured. In other embodiments, the phantom is designed for calibration in general (e.g., for different imaging systems, different applications, or different technicians), but is designed for this general calibration.

In additional or alternative embodiments, the phantom is used for other processes. For example, a resolution of the imaging system as configured in one way may be tested. Patterns of different size or scale are included in the phantom. By scanning the phantom with the medical imaging system, the resolution may be determined based on the size of the patterns that may be distinguished in the scan data. As another example, different phantoms or a phantom with different characteristics is used to determine whether imaging artifacts result. The characteristics of the imaging artifacts may be measured or identified so that the imaging artifacts may be avoided (e.g., re-configure the medical imaging system) or reduced. The structures that cause the imaging artifacts may be tested by inclusion in the phantom. In yet another example, the phantom is contrasted for comparison with scan results to confirm results of surgical intervention.

Figure 2:
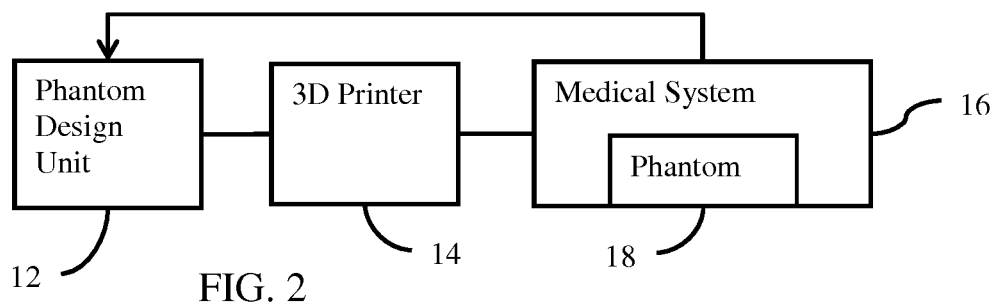
FIG. 2 shows an example of system for three-dimensional printing of a medical imaging phantom with feedback to vary design.

FIG. 2 shows a system of one embodiment for three-dimensionally printing a medical imaging phantom. The system implements the method of FIG. 1 or a different method. Since three-dimensional printing is being used, the phantom may be designed as needed for a single purpose, such as for calibrating for a given patient, calibrating for a given medical imaging system, calibrating for a particular technician, calibrating for specific research, or for other unique purpose. Rather than a phantom designed to operate with many medical imaging systems for any technician to calibrate for all patients, the phantom may be modified or created from scratch with unique alterations or differences as desired. In alternative embodiments, a phantom for generalized use across patients, medical imaging systems, and/or technicians is designed, printed and used.

The system includes a phantom design unit 12, a three-dimensional printer 14, a medical imaging system 16, and a phantom 18. Additional, different, or fewer components may be provided. For example, the medical imaging system 16 is not provided. As another example, additional medical imaging systems 16 for use with the same or different phantoms 18 are provided.

The phantom design unit 12 is a computer assisted design (CAD) workstation, computer or server. A processor of the phantom design unit 12 generates a user interface for selecting among phantom options, selecting a phantom, and/or designing a phantom from scratch.

The three-dimensional printer 14 is any now know or later developed three-dimensional printer. A reservoir or reservoirs of plastic, metal, ceramic, and/or other material connects with a deposit head. Under the control of a controller, the deposit head and/or a support platform are moved to add successive material in layers, building up the three-dimensional construction until a physical three-dimensional phantom is created. Any additive manufacturing system may be used. The three-dimensional printer 14 is configured by the instructions implemented by the controller using the print file for the phantom to construct the medical imaging phantom. The user defined (e.g., by selection in computer assisted design) phantom is built.

The medical system 16 is any now known or later developed medical imaging system or scanner. For example, the medical system 16 is a CT or other x-ray system (e.g., fluoroscopic). An x-ray source and detector are positioned opposite each other and adjacent to a patient and may be moved about the patient for scanning. In one embodiment, the medical system 16 is a spiral or C-arm CT system. In other examples, the medical system 16 is a MR, PET, ultrasound, SPECT, or other imaging system for scanning a patient.

The medical system 16 is configured by stored settings and/or by user selected settings to scan the phantom 18. The scan occurs by transmitting and receiving or by receiving alone. By positioning relative to the phantom, aiming, and/or detecting, the phantom is scanned. The scan data resulting from the scan may be reconstructed, image processed, rendered, or otherwise processed to show an image and/or calculate a characteristic of the phantom. For example, a volume, area, distance, or other quantification is calculated and compared against the known value associated with the phantom for calibration. As another example, an image is analyzed to determine the existence of one or more imaging artifacts associated with a texture, pattern or other characteristic of the phantom.

The phantom 18 is plastic, metal, resin, ceramic, other material, or combinations thereof. The phantom 18 has any shape, size, structure, insert, texture, pattern, or combinations thereof. For example, a plastic geometric shape includes one or more inserts of denser plastic, metal, plastic with added molecules (e.g., iodine), or other material. As another example, an organ shaped phantom 18 is provided with one or more structures or patterns emulating one or more specific organ pathologies.

In the example of FIG. 2, a feedback loop from the medical imaging system to the phantom design unit 12 is shown. The feedback allows for refinement or modification of a phantom design based on medical scan results. Since a three-dimensional printer 14 is used, the phantom may be easily remade with modifications so that the desired phantom is provided. In alternative embodiments, the feedback is not provided and/or is not used.

For feedback, the organ phantom or other phantom 18 is scanned with the medical imaging system 16. The medical imaging system 16 is configured for any scan, such as a scan specific or as planned for a patient or research.

The feedback of the scan data or information derived from the scan data is then used to alter a print file defining the organ phantom or other phantom 18. The print file is altered in response to the scan data. The print file is as formatted for three-dimensional printing, for computer assisted design, or for a phantom design application.

The print file is altered by changing the model for the phantom 18. Inserts may be added or removed. The pathology incorporated may be altered. Edges may be moved. Locations of inserts or structure may be moved. Any of the optional selections may be re-made. Positions may be changed, such as translating, rotating, and/or scaling an edge, structure, insert, or pattern. Manual, automatic, or semi-automatic alteration may be provided.

In one example, a mesh representing the phantom is altered. The mesh may be a segmentation from a medical scan of a patient. The mesh is then used in an iterative process to create a desired organ phantom. A transformation resulting in a change for the targeted manipulation is applied. One or more parts of the mesh or surfaces are altered.

The corrected phantom model is then formed or incorporates the changes for printing. The model is then formatted for three-dimensional printing. The corrected or altered print file is used to re-print the phantom (e.g., organ phantom). The three-dimensional printer 14 prints the altered phantom 18. This altered phantom 18 is scanned by the medical system 16 for calibration and/or to test the alteration.

Another use for a three-dimensionally printed phantom is to measure radiation dose for radiotherapy. For example, a phantom is created from the actual patient anatomy. Then sensors are inserted into the phantom, and the phantom is put into the treatment region. The treatment is applied to the phantom in the treatment region. In this way, the dosage to be applied to the tumor is verified by measurements from the sensors in the phantom. The phantom may include surrounding tissue to measure dosage for avoiding radiation in the surrounding tissues. In other embodiments, the phantom is created using "dose-sensitive" material that would be altered by the radiation. The measurement is by visible change to the phantom.

Figure 3:
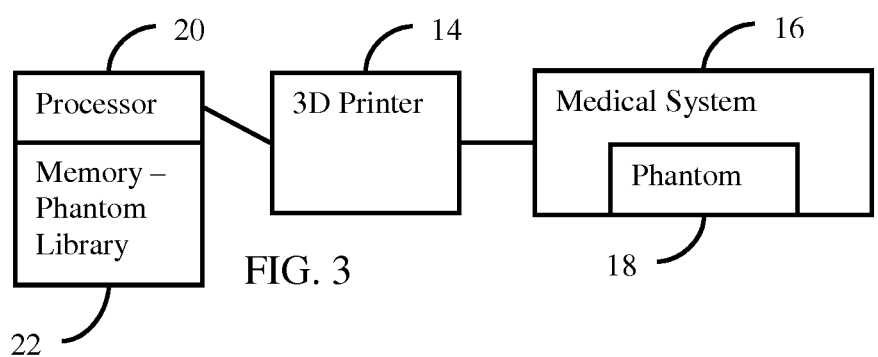
FIG. 3 is a block diagram of one embodiment of a system for three-dimensional printing of a medical imaging phantom.

FIG. 3 shows the system of FIG. 2, but without the feedback. Feedback may be used. In FIG. 3, the phantom design unit 12 is represented as a processor 20 and memory 22. The processor 20 and memory 22 are part of a computer, such as a workstation or server for receiving user input of selections of a phantom and/or characteristics of a phantom.

Additional, different, or fewer components may be provided. For example, a user input is provided. As another example, a communications network between the processor 20 and the memory 22 is provided where the memory 22 is part of a remote database. In one example, the processor 20 is part of the medical system 16 or the user interface for design is implemented on the medical system 16, allowing for medical system local design of the phantom. The three-dimensional printer 14 is in the same facility or is operated by a service that ships the designed phantom 18 to the healthcare facility having the medical system 16.

The memory 22 is a graphics processing memory, video random access memory, random access memory, system memory, cache memory, hard drive, optical media, magnetic media, flash drive, buffer, database, combinations thereof, or other now known or later developed memory device for storing print files, phantom models, and/or options for phantoms. The memory 22 is part of the imaging system 16, a computer associated with the processor 20, a database, another system, a picture archival memory, or a standalone device.

The memory 22 is configured by the processor 20 to store a definition of the medical imaging phantom. A model or print file defining the phantom 18 as designed or otherwise selected is stored by the memory 22.

A library of different options for the medical imaging phantom may be stored in the memory 22. For example, the memory 22 stores models or print files for different available or pre-designed, complete phantoms 18 for selection. As another example, the memory 22 stores different characteristics or other selectable options for altering a pre-designed, complete phantom 18. In another example, the memory 22 stores different options useable to design the phantom 18 from scratch or without starting with a pre-designed, complete phantom 18. The different options for designing form scratch or altering a pre-design may include pathologies, patterns, densities, inserts, structure, locations thereof within the phantom 18, size thereof and/or of the phantom itself, starting phantoms, templates, or combinations thereof. By the user selecting various options for the phantom 18, a definition of the phantom is formed. In alternative embodiments, the memory 22 stores a model or print file for only one phantom 18.

The memory 22 may store both models and print files for the phantom 18 and/or options. For example, the user selects a model. A corresponding print file is also provided in the memory 22. If the user alters the model by selection of other options, then the print file is likewise altered or a corresponding print file being stored is selected. Alternatively, the memory 22 only stores the print file or only the model (e.g., the processor 20 creates the print file after the model is designed).

The memory 22 or other memory is alternatively or additionally a computer readable storage medium storing data representing instructions executable by the programmed processor 20 for creating a medical imaging phantom for three-dimensional printing. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts, or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 20 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for creating a phantom model for three-dimensional printing. The processor 20 is a single device or multiple devices operating in serial, parallel, or separately. The processor 20 may be a main processor of a computer, such as a laptop or desktop computer, or may be a processor for handling some tasks in a larger system, such as in the medical imaging system 16 or the three-dimensional printer 14. The processor 20 is configured by instructions, design, firmware, hardware, and/or software to perform the acts discussed herein.

In one embodiment using segmentation from scan data of a patient to create an organ phantom 18, the processor 20 is configured to segment the organ of the patient from a medical scan. Data representing the patient volume is processed to find locations and/or surfaces of anatomic structures or parts of anatomic structures. Any segmenting may be used. The segmenting itself provides a surface or mesh for the anatomy. Alternatively, the located anatomy is used to create the mesh or surface.

The processor 20 is configured to create a model for three-dimensional printing from the segmented structure. The model may be created directly by fitting a pre-determined model to the segmented structure. Cost functions or limitations on the fitting may be used to preserve 3D printing characteristics (e.g., a stand) while shaping the anatomy portion to the segmented organ. Alternatively, the processor determines a transform between the segmented structure and a template structure, such as a mesh derived from an average anatomy, anatomy of a different patient, or a model of anatomy. The transform is the warping or non-rigid distortion to convert the template structure into the patient specific organ. That transform is then applied to a model for three-dimensional printing. The model for three-dimensional printing is based on the template structure or mesh converted into a three-dimensional print model (e.g. orient, add base, add supporting or strengthening structure, and/or optimize material usage). The model is transformed. The transformation warps the model for three-dimensional printing to simulate the segmented anatomy of the patient. The result is a transformed model for three-dimensional printing that represents the patient-specific anatomy. This patient-specific anatomy is used as a phantom 18 for scanning.

In alternative embodiments, the processor 20 accesses a plurality of models previously created from segmentations from other patients. The processor 20 interacts with the user for selection of a specific one of the segmentation models to create a phantom.

In another embodiment, the processor 20 accesses a plurality of models created without segmentation from actual scans of patients. Instead, pre-designed or other models of phantoms are provided. The processor 20 is used to select the desired phantom model. Alternatively, the processor 20 is used to design a phantom without segmentation and without pre-design.

The processor 20 may be used to alter an existing phantom model or to create a phantom model. One or more options are presented to the user by the processor 20. In response, the user selects various options. The processor 20 receives the selections to form the phantom model. A template may be used for creating the model. The processor 20 combines the selections to create a model of the phantom.

The processor 20 creates a print file from the model. The phantom model is reformatted into a file useable by the three-dimensional printer 14. Alternatively, the model data is sent to the three-dimensional printer 14, and the three-dimensional printer 14 reformats for printing the phantom 18.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for three-dimensional printing of a medical imaging phantom, the method comprising:
   receiving, using a database, a selection of an organ phantom from a library of organ phantoms;
   three-dimensionally printing, with a three-dimensional printer, the selected organ phantom; and
   calibrating a medical imaging system with the three-dimensionally printed organ phantom.

2. The method of claim 1 wherein receiving comprises receiving the selection as a type of organ where the library includes a plurality of the types of organs represented in a three-dimensional printing format.

3. The method of claim 1 wherein receiving comprises receiving the selection as a first organ where the library includes a plurality of organs of a same type as the first organ, each of the organs of the plurality, including the first organ, having different pathology.

4. The method of claim 1 wherein receiving comprises receiving the selection as the organ phantom with a first insert, the library including a plurality of selectable inserts including the first insert.

5. The method of claim 4 wherein receiving the selection comprises receiving the selection with the plurality of inserts comprising an unnatural shape for an organ represented by the organ phantom.

6. The method of claim 4 wherein receiving the selection comprises receiving the selection with the plurality of inserts comprising natural pathologies for an organ represented by the organ phantom.

7. The method of claim 1 wherein receiving comprises receiving the selection as of the organ phantom with selected size, thickness, texture, or combinations thereof.

8. The method of claim 1 wherein the selected organ phantom is defined with layers of anatomic structure, and wherein three-dimensionally printing comprises printing the layers.

9. The method of claim 1 wherein the selected organ phantom is defined with one or more densities, and wherein three-dimensionally printing comprises printing the printed organ phantom as having the one or more densities.

10. The method of claim 1 further comprising:
    scanning the organ phantom with the medical imaging system;
    altering a print file defining the organ phantom in response to scan data from the scanning; and
    re-printing the organ phantom with the altered print file.

11. The method of claim 1 wherein receiving comprises receiving the selection as the organ phantom based on a segmentation from a medical scan.

12. The method of claim 1 wherein calibrating comprises scanning the printed organ phantom and altering a setting of the medical imaging system based on results of the scanning.

13. A method for three-dimensional printing of a medical imaging phantom, the method comprising:
    receiving, using a database, a selection of an organ phantom from a library of organ phantoms;
    three-dimensionally printing, with a three-dimensional printer, the selected organ phantom; and
    calibrating a medical imaging system with the three-dimensionally printed organ phantom, wherein calibrating comprises determining a resolution using the printed organ phantom, identifying a characteristic of an imaging artifact using the printed organ phantom, configuring the medical imaging system for quantitative measurements using the printed organ phantom, or combinations thereof.

14. The method of claim 13 wherein receiving comprises receiving the selection as a type of organ where the library includes a plurality of the types of organs represented in a three-dimensional printing format.

15. The method of claim 13 wherein receiving comprises receiving the selection as a first organ where the library includes a plurality of organs of a same type as the first organ, each of the organs of the plurality, including the first organ, having different pathology.

16. The method of claim 13 wherein receiving comprises receiving the selection as the organ phantom with a first insert, the library including a plurality of selectable inserts including the first insert, the plurality of inserts comprising an unnatural shape for an organ represented by the organ phantom.

17. The method of claim 13 wherein receiving comprises receiving the selection as of the organ phantom with selected size, thickness, texture, or combinations thereof.

18. The method of claim 13 wherein the selected organ phantom is defined with layers of anatomic structure and/or one or more densities, and wherein three-dimensionally printing comprises printing the layers and/or having the one or more densities.

19. The method of claim 13 further comprising:
scanning the organ phantom with the medical imaging system;
altering a print file defining the organ phantom in response to scan data from the scanning; and
re-printing the organ phantom with the altered print file.

* * * * *